US00PP15497P2

(12) United States Plant Patent
Friday

(10) Patent No.: US PP15,497 P2
(45) Date of Patent: Jan. 25, 2005

(54) PEACH TREE NAMED 'P.F. LUCKY 21'

(50) Latin Name: *Prunus persica*
Varietal Denomination: P.F. Lucky 21

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 0 days.

(21) Appl. No.: 10/702,925

(22) Filed: Nov. 7, 2003

(51) Int. Cl.[7] ..... A01H 5/00

(52) U.S. Cl. ..... Plt./198

(58) Field of Search ..... Plt./198

(56) References Cited

U.S. PATENT DOCUMENTS

PP14,778 P3 * 5/2004 Friday ..... Plt./198

OTHER PUBLICATIONS http://www.gov.on.ca/OMAFRA/english/crops/hort/news/tenderfr/tf0801a2.htm.*

* cited by examiner

*Primary Examiner*—Kent Bell
*Assistant Examiner*—W C Haas

(57) ABSTRACT

A new and distinct variety of peach, *Prunus persica,* tree having the following unique combination of desirable features:

1. Producing a very firm fruit that can best be described as "crunchy" when bitten into when firm ripe.
2. The limbs of the tree naturally grow at wide angles creating a wide-spreading tree.
3. A substantially spherical fruit with yellow flesh having light red around the pit.
4. A mid-season peach variety that matures after 'Redhaven' (unpatented) and which hangs on the tree for many days staying extremely firm.
5. A peach variety that has excellent storage and shelf life.

1 Drawing Sheet

Botanical classification: *Prunus persica.*
Variety designation: 'P.F. Lucky 21'.

ORIGIN OF VARIETY

The new peach tree {hereinafter referred to as the 'P.F. Lucky 21' peach tree} was originated by Paul Friday in an experimental orchard, which is maintained for the purposes of breeding peach trees, in Coloma, Mich. Coloma is located in the southwest section of Michigan, in USDA Hardiness Zone 6a.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollinations of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, 'P.F. Lucky 21', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in the experimental orchard, located in Coloma, Mich. The asexual propagation demonstrates that such reproduction of the characteristics of the tree are consistant and are established and transmitted through succeeding propagation.

SUMMARY OF THE VARIETY

The new and distinct variety of peach tree is of semi-dwarf, moderate upright growth and a regular and productive bearer of peaches. A distinct characteristic of the 'P.F. Lucky 21' peach tree is its medium vigor having very stubby new growth with short internodes. The nodes are generally ½ inch apart on the new growth. The blossoms bloom in mid-season and are characterized by being contracted or partially spread in a 1-inch diameter during full bloom. At the same time the petals of the blossoms are of lesser length than the length of petals of the normal showy blossom as exemplified by the 'Loring' {unpatented} peach blossom.

The flesh of the fruit of the present peach tree is firm and is yellow.

The skin is smooth having moderate to little down and is of dark red color over about one hundred percent (100%) of its surface at maturity. At maturity the peach is spherical having an average diameter of about 2⅞".

The fruit has a firm flesh and may be described as resilient to the extent that the flesh is yieldable and restorable to its original state when subjected to impact forces which may cause bruising and soft blemishes which lead to rejection by the buyer in the fresh market in peaches of the commercial varieties. The firmness of the fruit facilitates handling and packaging of the peaches without damaging the same for shipment. This results in less spoilage and also increases the shelf life.

The fruit matures in the earlier part of the peach growing season of southwestern Michigan. The fruit as mentioned heretofore is of red color over about one hundred percent (100%) of its surface and has a very attractive appearance.

BRIEF DESCRIPTION OF THE PHOTOGRAPHS

The top photograph shows four (4) whole fruit with one fruit bisected across the axis showing the slight red coloration of flesh from the pit well. The otherwise clear flesh is also shown. A tape measure is included to show the excellent size of this fruit.

The bottom photograph shows the leaves of the plant, depicting both upper and lower sides, length of the leaves, and internode length.

DESCRIPTION OF VARIETY

The detailed botanical description of the foliage and fruit of the new variety of peach tree is based upon observations of a speciment, as grown on its own roots, in typical outdoor conditions grown at Coloma, Mich., USDA Zone 6a with the color terminology, other than the terminology expressed in common terms, in accordance with the Pantone Matching System (PMS) as used internationally to identify printed colors.

Botanical classification: *Prunus persica* cultivar 'P.F. Lucky 21'.

Tree:
- *Age.*—Seven (7) years.
- *Height.*—Unpruned 14'.
- *Width.*—Unpruned 14'.
- *Size.*—Medium.
- *Vigor.*—Medium.
- *Density of leaves.*—Medium.
- *Form.*—Spreading.
- *Production.*—Good, the tree produces about 1½ bushels of fruit per year per tree.
- *Bearer.*—Heavy, must be thinned.
- *Disease resistance to bacterial leaf and fruit spot.*—Very resistant.

Trunk:
- *Bark.*—Dark Gray (410).
- *Surface.*—Somewhat rough.
- *Diameter.*—3¼" at 18" above ground at 7 years of age.
- *Lenticels.*—Pronounced.
- *Lenticels color.*—481.
- *Lenticels size.*—⅛" to ⅜".

Branches:
- *Size.*—Medium 2⅝" diameter.
- *Branch color.*—Gray (408).
- *Surface.*—Somewhat rough.
- *Lenticels per square inch.*—Eight (8).
- *Lenticels color.*—472.
- *Lenticels size.*—⅛ inch to ⅜ inch.
- *Crotch angles.*—80 degree angles.
- *Internode length.*—Noteably short about ½ inch in length.

Leaves:
- *Size.*—Average length 6" — average width 1⁷⁄₁₆".
- *Form.*—Lanceolate — pointed.
- *Base.*—Acute.
- *Apex.*—Pointed.
- *Thickness.*—Medium.
- *Texture.*—Glabrous.
- *Margin.*—Finely serrated.
- *Petiole length.*—⁷⁄₁₆".
- *Gland number.*—1 to 2 on each side of leaf base.
- *Gland color.*—Dark red.
- *Gland shape.*—Round cupped.
- *Leaf color.*—Upper surface green (371) — lower surface green (385).

Flower buds:
- *Size.*—½ inch long — ⅜ inch wide.
- *Bud shape.*—Ovoid.
- *Color.*—211.

Flowers:
- *Blooming period.*—Apr. 25, 2003 to Apr. 30, 2003.
- *Bloom size.*—1 inch diameter.
- *Size of petals.*—½ inch long — ³⁄₁₆ inch wide.
- *Number of petals.*—Five (5).
- *Shape of petals.*—Cupped.
- *Petal color.*—250.
- *Sepal size.*—¼ inch long — ³⁄₁₆ inch wide.
- *Sepal shape.*—Cupped.
- *Sepal color.*—384.
- *Number of anthers.*—24.
- *Anthers color.*—417.
- *Number of stamens.*—24.
- *Stamen length.*—⅜".
- *Stamen color.*—133.
- *Pistil length.*—⁵⁄₁₆".
- *Pistil color.*—380.
- *Pollen.*—Present, self fertilizing.
- *Flower color.*—250.
- *Flowers per cluster.*—Two (2).
- *Fragrance.*—Strong.

Fruit:
- *Maturity when described.*—Firm ripe.
- *Date of first picking.*—Aug. 22, 2003.
- *Date of last picking.*—Sep. 5, 2003.
- *Size.*—Average 2⅞ inch diameter.
- *Form.*—Spherical.
- *Suture.*—Not pronounced, stays very firm.
- *Weight.*—Average 7.5 oz.

Skin:
- *Thickness.*—Medium.
- *Texture.*—Medium.
- *Tendency to crack.*—None.
- *Down.*—Light.
- *Color.*—Red (201).

Flesh:
- *Texture.*—Extremely firm, nonmelting, free of fiber.
- *Ripen.*—Evenly.
- *Flavor.*—Very Good.
- *Aroma.*—Pleasant.
- *Eating quality.*—Very good.
- *Color.*—116.
- *Pit cavity color.*—186.

Stone:
- *Type.*—Very freestone.
- *Size.*—1½" long — 1" wide — ¾" thick.
- *Form.*—Ovoid.
- *Base.*—Straight.
- *Apex.*—Elongated point.
- *Sides.*—Uneven, a pronounced suture on one side.
- *Surface.*—Irregularly furrowed.
- *Color.*—Brown (470).

*Tendency to crack.*—Slight.

*Kernel.*—¾" long — 7/16" wide — ⅛" thick.

Use: Dessert.

Shipping quality: Excellent.

Keeping quality: Excellent.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree as herein illustrated and described.

* * * * *

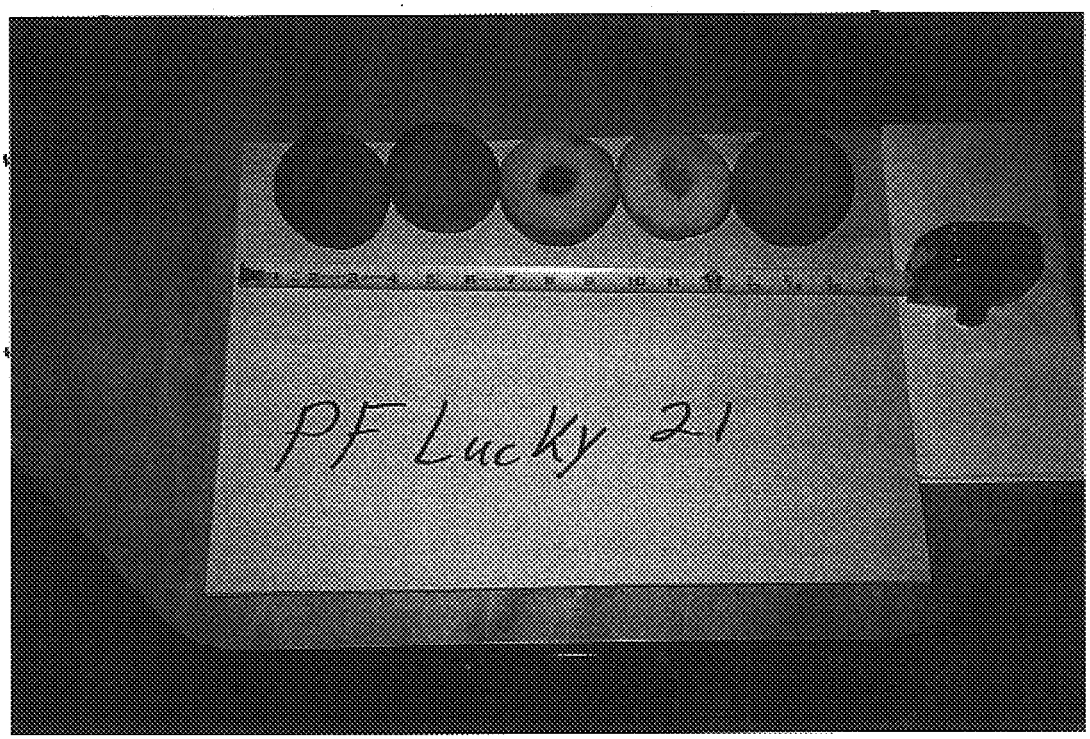
PF Lucky 21
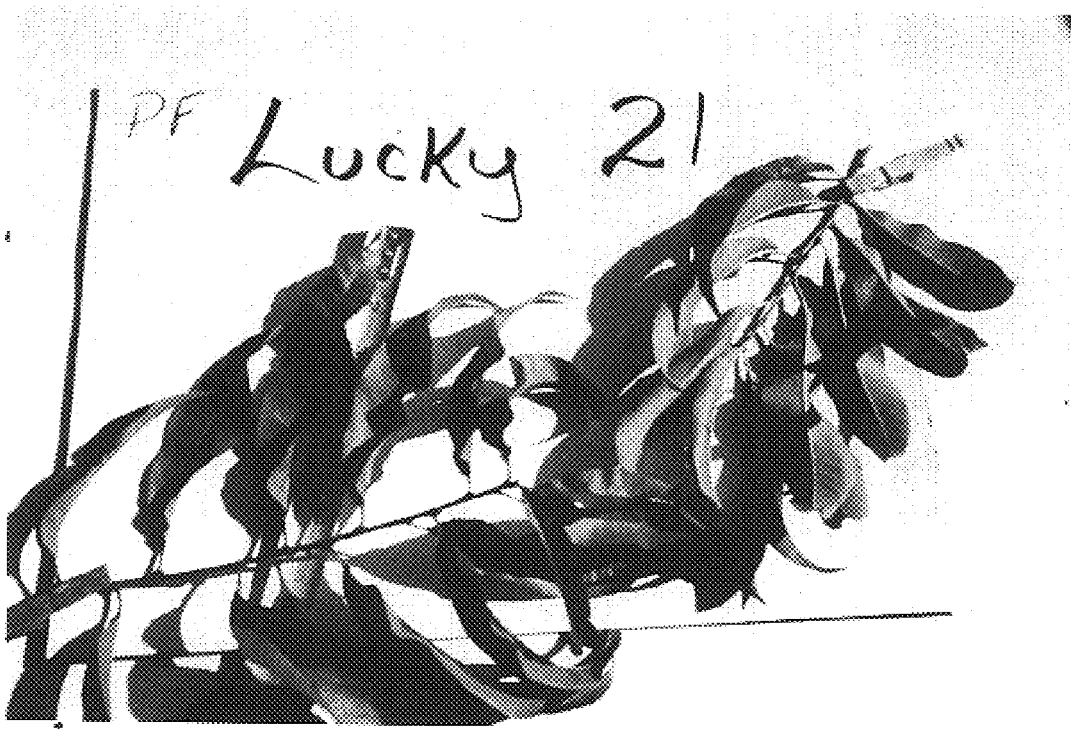
PF Lucky 21